United States Patent
Hacker

(10) Patent No.: US 6,472,076 B1
(45) Date of Patent: Oct. 29, 2002

(54) DEPOSITION OF ORGANOSILSESQUIOXANE FILMS

(75) Inventor: Nigel P. Hacker, Palo Alto, CA (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 09/420,218

(22) Filed: Oct. 18, 1999

(51) Int. Cl.$^7$ .................................................. B32B 9/00
(52) U.S. Cl. ........................ 428/447; 428/319.1; 427/58; 427/255.36; 427/255.392; 427/402; 427/387; 427/577; 528/31; 524/267; 524/731
(58) Field of Search ............................... 428/304.4, 319.1, 428/319.9, 336, 447; 427/575, 58, 255.36, 255.392, 402, 387, 577; 528/21, 31; 524/267, 731

(56) References Cited

U.S. PATENT DOCUMENTS

| | | | |
|---|---|---|---|
| 2,637,718 A | 5/1953 | Rust .......................... 260/46.5 |
| 3,615,272 A | 10/1971 | Collins et al. ............... 423/325 |
| 4,026,868 A | 5/1977 | Merrill ....................... 260/46.5 |
| 4,239,811 A | * 12/1980 | Kemlage |
| 4,399,266 A | 8/1983 | Matsumura et al. .......... 528/10 |
| 4,609,751 A | 9/1986 | Hajjar ......................... 556/456 |
| 4,624,870 A | 11/1986 | Anthony ..................... 427/387 |
| 4,626,556 A | 12/1986 | Nozue et al. .................. 522/99 |
| 4,670,299 A | 6/1987 | Fukuyama et al. ............ 427/96 |
| 4,694,040 A | 9/1987 | Hashimoto et al. .......... 524/765 |
| 4,723,978 A | 2/1988 | Clodgo et al. ................. 65/31 |
| 4,749,631 A | 6/1988 | Haluska et al. .............. 428/704 |
| 4,753,855 A | 6/1988 | Haluska et al. .............. 428/702 |
| 4,756,977 A | 7/1988 | Haluska et al. |
| 4,808,653 A | 2/1989 | Haluska et al. .............. 524/398 |
| 4,822,697 A | 4/1989 | Haluska et al. .............. 428/698 |
| 4,847,162 A | 7/1989 | Haluska et al. .............. 428/457 |
| 4,849,296 A | 7/1989 | Haluska et al. .............. 428/457 |
| 4,895,914 A | 1/1990 | Saitoh et al. ................. 525/478 |
| 4,898,907 A | 2/1990 | Haluska et al. .............. 524/490 |
| 4,911,992 A | 3/1990 | Haluska et al. .............. 428/698 |
| 4,973,526 A | 11/1990 | Haluska ....................... 428/697 |
| 4,999,397 A | 3/1991 | Weiss et al. .................. 524/755 |
| 5,008,320 A | 4/1991 | Haluska et al. .............. 524/361 |
| 5,010,159 A | 4/1991 | Bank et al. |
| 5,045,592 A | 9/1991 | Weiss et al. .................. 524/755 |
| 5,047,492 A | 9/1991 | Weidner et al. ................ 528/15 |
| 5,059,448 A | 10/1991 | Chandra et al. ............ 427/53.1 |
| 5,063,267 A | 11/1991 | Hanneman et al. .......... 524/284 |

(List continued on next page.)

FOREIGN PATENT DOCUMENTS

| | | |
|---|---|---|
| CA | 2100278 | 1/1994 |
| DE | 196 08 904 A1 | 9/1996 |
| EP | 0 270 229 A2 A3 | 6/1988 |

(List continued on next page.)

OTHER PUBLICATIONS

K.A. Andrianov, et al., entitled "Hydrolytic Poly–Condensation of Higher Alkyltrichlorosilanes" dated 1967, pp. 435–441.

(List continued on next page.)

*Primary Examiner*—Blaine Copenheaver
*Assistant Examiner*—Leanna Roché
(74) *Attorney, Agent, or Firm*—Rutland & Tucker, LLP; Sandra P. Thompson

(57) ABSTRACT

There is provided an array of alkyl substituted silsesquioxane thin film precursors having a structure wherein alkyl groups are bonded to the silicon atoms of a silsesquioxane cage. The alkyl groups may be the same as, or different than the other alkyl groups. In a first aspect, the present invention provides a composition comprising a vaporized material having the formula $[R-SiO_{1.5}]_x[H-SiO_{1.5}]_y$, wherein $x+y=n$, n is an integer between 2 and 30, x is an integer between 1 and n and y is a whole number between 0 and n. R is a $C_1$ to $C_{100}$ alkyl group. Also provided are films made from these precursors and objects comprising these films.

18 Claims, 3 Drawing Sheets

Where R, $R_1$, $R_2$, $R_3$, $R_4$, $R_5$, $R_6$, and $R_7$ = alkyl

U.S. PATENT DOCUMENTS

| | | | |
|---|---|---|---|
| 5,085,893 A | 2/1992 | Weiss et al. | 427/387 |
| 5,091,162 A | 2/1992 | Frye et al. | 423/325 |
| 5,106,604 A | 4/1992 | Agaskar | 423/325 |
| 5,116,637 A | 5/1992 | Baney et al. | 427/340 |
| 5,118,530 A * | 6/1992 | Hanneman et al. | |
| 5,145,723 A | 9/1992 | Ballance et al. | 427/397.7 |
| 5,165,955 A | 11/1992 | Gentle | 427/575 |
| 5,183,684 A | 2/1993 | Carpenter | 427/574 |
| 5,210,168 A | 5/1993 | Bergstrom et al. | 528/12 |
| 5,238,787 A | 8/1993 | Haluska et al. | 430/325 |
| 5,258,334 A | 11/1993 | Lantz, II | 437/238 |
| 5,262,201 A | 11/1993 | Chandra et al. | 427/376.2 |
| 5,279,661 A | 1/1994 | Gentle | |
| 5,283,545 A | 2/1994 | Pernisz | 338/308 |
| 5,290,354 A | 3/1994 | Haluska | 106/479 |
| 5,293,335 A | 3/1994 | Pernisz et al. | 365/148 |
| 5,310,583 A | 5/1994 | Eckstein et al. | 427/575 |
| 5,312,684 A | 5/1994 | Michael et al. | 428/336 |
| 5,320,868 A | 6/1994 | Ballance et al. | |
| 5,336,532 A | 8/1994 | Haluska et al. | 427/515 |
| 5,348,839 A | 9/1994 | Haluska et al. | 430/270 |
| 5,370,903 A | 12/1994 | Mine et al. | 427/126.2 |
| 5,370,904 A | 12/1994 | Mine et al. | 427/126.2 |
| 5,372,842 A | 12/1994 | Mine et al. | 427/126.2 |
| 5,380,567 A | 1/1995 | Haluska | 427/578 |
| 5,416,190 A | 5/1995 | Mine et al. | 528/492 |
| 5,436,029 A | 7/1995 | Ballance et al. | 427/126.2 |
| 5,441,765 A | 8/1995 | Ballance et al. | 427/228 |
| 5,445,894 A | 8/1995 | Ballance et al. | 427/228 |
| 5,446,088 A | 8/1995 | Haluska | 524/588 |
| 5,486,564 A | 1/1996 | Mine et al. | 524/588 |
| 5,523,163 A | 6/1996 | Ballance et al. | 428/446 |
| 5,540,948 A | 7/1996 | Haluska | 427/96 |
| 5,547,703 A | 8/1996 | Camilletti et al. | 427/126.3 |
| 5,609,925 A | 3/1997 | Camilletti et al. | 427/503 |
| 5,618,878 A | 4/1997 | Syktich et al. | 524/588 |
| 5,635,240 A | 6/1997 | Haluska et al. | 427/180 |
| 5,660,895 A * | 8/1997 | Lee et al. | |
| 5,670,596 A | 9/1997 | Razzano et al. | 528/16 |
| 5,707,681 A | 1/1998 | Bremmer et al. | 427/58 |
| 5,707,683 A | 1/1998 | Currie et al. | 427/126.2 |
| 5,853,808 A | 12/1998 | Arkles et al. | 427/377 |
| 5,858,544 A | 1/1999 | Banaszak Holl et al. | 428/447 |
| 5,859,162 A | 1/1999 | Yamamoto et al. | 528/31 |
| 5,859,168 A | 1/1999 | Yamamoto et al. | 528/31 |
| 5,866,197 A * | 2/1999 | Bremmer et al. | |
| 5,906,859 A * | 5/1999 | Bremmer et al. | |
| 6,015,457 A * | 1/2000 | Leung et al. | |
| 6,107,505 A | 8/2000 | Yoshida et al. | 556/450 |
| 6,191,183 B1 * | 2/2001 | Kobayashi et al. | |
| 6,197,913 B1 * | 3/2001 | Zhong | |
| 6,211,071 B1 * | 4/2001 | Lukanc et al. | |

FOREIGN PATENT DOCUMENTS

| | | |
|---|---|---|
| EP | 0 270 231 A2 A3 | 6/1988 |
| EP | 0 270 263 A2 A3 | 6/1988 |
| EP | 0 720 369 A2 A3 | 6/1988 |
| EP | 0 323 103 A2 | 7/1989 |
| EP | 0 323 186 A2 | 7/1989 |
| EP | 0 410 564 A2 A3 | 1/1991 |
| EP | 0 419 076 A1 | 3/1991 |
| EP | 0 427 395 A1 | 5/1991 |
| EP | 0659904 A2 * | 5/1991 |
| EP | 0493879 A1 * | 11/1991 |
| EP | 0 462 715 A1 | 12/1991 |
| EP | 0 461 782 A2 A3 | 12/1991 |
| EP | 0464836 A2 | 1/1992 |
| EP | 0 466 205 A1 | 1/1992 |
| EP | 0 493 879 A2 A3 | 7/1992 |
| EP | 0 510 872 A1 | 10/1992 |
| EP | 0 512 717 A2 A3 | 11/1992 |
| EP | 0 516 144 A1 | 12/1992 |
| EP | 0 516 308 A1 | 12/1992 |
| EP | 0 560 485 A1 | 9/1993 |
| EP | 0 576 166 A2 | 12/1993 |
| EP | 0 596 678 A2 | 5/1994 |
| EP | 0 599 209 A2 A3 | 6/1994 |
| EP | 0 604 779 A1 | 7/1994 |
| EP | 0 606 580 A1 | 7/1994 |
| EP | 0 606 588 A1 | 7/1994 |
| EP | 0 615 000 A1 | 9/1994 |
| EP | 0 616 001 A1 | 9/1994 |
| EP | 0624591 A1 | 11/1994 |
| EP | 0 652 246 A1 | 5/1995 |
| EP | 0 686 680 A1 | 12/1995 |
| EP | 0 725 103 A2 A3 | 8/1996 |
| EP | 0764704 A1 * | 3/1997 |
| EP | 0883164 A2 | 12/1998 |
| GB | 2 199 817 A | 7/1988 |
| JP | 52-31854 | 8/1977 |
| JP | 53-88099 | 8/1978 |
| JP | 55-111148 | 8/1980 |
| JP | 56-139533 | 10/1981 |
| JP | 57-112047 | 7/1982 |
| JP | 58-003249 | 1/1983 |
| JP | 58-066335 | 4/1983 |
| JP | 59-109565 | 6/1984 |
| JP | 59-189126 | 10/1984 |
| JP | 59-190211 | 10/1984 |
| JP | 60-42426 | 3/1985 |
| JP | 60-86017 | 5/1985 |
| JP | 60-124943 | 7/1985 |
| JP | 61-029153 | 2/1986 |
| JP | 61-127732 | 6/1986 |
| JP | 61-292342 | 12/1986 |
| JP | 2-277255 | 11/1990 |
| JP | 3-6845 | 1/1991 |
| JP | 3-227321 | 10/1991 |
| JP | 4-252228 | 9/1992 |
| JP | 4-252229 | 9/1992 |
| WO | WO 97/10282 | 3/1997 |

OTHER PUBLICATIONS

V.P. Korchkov, et al., entitled "Low Temperature Dielectric Films from Octavinylsilsesquioxane" dated 1982, pp. 373–376.

Gion Calzaferri, et al. entitled Structural and Vibrational Properties of the Octanuclear Silasesquioxane $C_6H_{13}(H_7Si_8O_{12})$ dated 1994, pp. 3123–3128.

Voronkov, et al. entitled "Peralkyloligohomosilsesquioxanes" dated 1992, pp. 557–563.

K.T. Nicholson, et al. entitled "Nanosegmented, hydrophobic Silicon Oxide Coatings for Metal Surfaces Based Upon Spherosiloxane Clusters" dated 2000, p. 329.

Martynova, et al. entitled "Preparation of Octakis" dated 1984, pp. 62–69.

Martynova entitled "Alkylsilsesquioxanes" dated Dec. 1981.

Lavrent' Ev, et al. entitled "Methylethyloctasilsesquioxanes as products of the reaction of ethylpolycyclosiloxanes with methyltrichlorosilane and their chromatographic–mass spectrometric study" dated 1981, pp. 124–130.

Olsson, *Arkiv. Kemi.* 13:367–78 (1958).

Barry et al., *J. Am Chem. Soc.* 77:4248–52 (1955).

Hendan et al., *J. Organomet. Chem.* 483:33–8 (1994).

Bolln et al., *Chem. Mater.* 9:1475–1479 (1997).

Bassindale et al., "Tailor–Made Silicon–Oxygen Compounds" Eds. Corriu et al., Vieweg, Wiesbaden, germany, pp. 171–176 (1995).
Calzaferri et al., *Helv. Chim. Acta* 74:1278–1280 (1991).
Herren et al., *Helv. Chim. Acta* 74:24–6 (1991).
Dittmar et al., *J. Organomet. Chem.* 489:185–194 (1995).
Rikowski et al., *Polyhedron* 16:3357–3361 (1997).
*Encyclopedia of Chemical Technology*, 4th Edition, John Wiley & Sons, Inc., 1995, vol. 14, p. 177.
Hacker, N., "Organic and Inorganic Spin–On Polymers for Low–Dielectic–Constant Applications," *MRS Bulletin*, vol. 22, No. 10, Oct. 1997, pp. 33–38.
Press Release, Applied Materials, "Applied Materials Announces Breakthrough Low K Dielectric Film for High-Speed Copper Chips", Nov. 6, 1998.

Dow Corning Corporation related to 3MS Product. Jan. 1, 1999.

"Black Diamond FTIR"—Figure 4. Semicon West. Jul. 12, 1999.

"Advanced Semiconductor Wafer Engineering"—Symposium. Apr. 5–7, 1999.

"Enabling low–k Material Integration Through Low–ion Plasma Dry Strip Processes", Qingyuan Han and Ivan L. Berry. *Micro Magazine*. Oct., 1999.

* cited by examiner

Where R = alkyl

Where R, $R_1$, $R_2$, $R_3$, $R_4$, $R_5$, $R_6$, and $R_7$ = alkyl

DEPOSITION OF ORGANOSILSESQUIOXANE FILMS

BACKGROUND OF THE INVENTION

Semiconductors are widely used in integrated circuits for electronic applications, including high-speed computers and wireless communications. Such integrated circuits typically use multiple transistors fabricated in single crystal silicon. Many integrated circuits now contain multiple levels of metallization for interconnections. A single semiconductor microchip may have thousands, and even millions of transistors. Logically, a single microchip may also have millions of lines interconnecting the transistors. As device geometries shrink and functional density increases, it becomes imperative to reduce the capacitance between the lines. Line-to-line capacitance can build up to a point where delay time and crosstalk hinders device performance. Reducing the capacitance within these multi-level metallization systems reduces the RC constant, crosstalk voltage, and power dissipation between the lines. Typically, thin films of silicon dioxide are used as dielectric layers and to reduce the capacitance between functional components of the device.

Such dielectric thin films serve many purposes, including preventing unwanted shorting of neighboring conductors or conducting levels, by acting as a rigid, insulating spacer; preventing corrosion or oxidation of metal conductors, by acting as a barrier to moisture and mobile ions; filling deep, narrow gaps between closely spaced conductors; and planarizing uneven circuit topography so that a level of conductors can then be reliably deposited on a film surface which is relatively flat. A significant limitation is that typically interlevel dielectric (ILD) and protective overcoat (PO) films must be fonned at relatively low temperatures to avoid destruction of underlying conductors. Another very important consideration is that such dielectric films should have a low relative dielectric constant k, as compared to silicon dioxide (k=3.9), to lower power consumption, crosstalk, and signal delay for closely spaced conductors.

Recently, attempts have been made to use materials other than silicon dioxide. Notable materials include low-density materials, such as aerogels and silsesquioxanes. The dielectric constant of a porous dielectric, such as a silicon dioxide aerogel, can be as low as 1.2. This lower dielectric constant results in a reduction in the RC delay time. However, methods of making aerogels require a supercritical drying step. This step increases the cost and the complexity of semiconductor manufacturing.

Films deposited from hydrogen silsesquioxane (HSQ) resins have been found to possess many of the properties desirable for ILD and PO applications. For example, Haluska et al. (U.S. Pat. No. 4,756,977, Jul. 12, 1988) describe a film deposition technique comprising diluting in a solvent a hydrogen silsesquioxane resin, applying this as a coating to a substrate, evaporating the solvent and ceramifying the coating by heating the substrate in air. Others have found that by ceramifying such a coating in the presence of hydrogen gas (Ballance et al., U.S. Pat. No. 5,320,868, Jun. 14, 1994) or inert gas (European Patent Application 90311008.8), the dielectric constant of the final film may be lowered and/or stabilized as compared to ceramifying in air. Each of these patents discloses the use of silsesquioxane resin dissolved in a solvent. The resulting silsesquioxane solution is coated onto a substrate by a spin-on coating technique.

Limited effort has been directed towards chemical vapor deposition of silsesquioxane dielectric coatings. See, Gentle, U.S. Pat. No. 5,279,661, Jan. 18, 1994 disclosing CVD of hydrogen silsesquioxane coatings on a substrate. Although these coatings form useful dielectric layers after curing, as device sizes progressively minimize, it is necessary to have available dielectric thin films having a lower dielectric constant than that provided by the simple hydrogen silsesquioxane films.

An array of low k thin films of different composition and precursors for these films which can be deposited onto a substrate using CVD would represent a significant advance in the art and would open avenues for continued device miniaturization. Quite surprisingly, the present invention provides such films and precursors.

SUMMARY OF THE INVENTION

It has now been discovered that silsesquioxanes having alkyl groups bonded to the silicon atoms of the silsesquioxane cage are useful precursors for low dielectric constant thin films. The alkylated silsesquioxane cages are easily prepared using art-recognized techniques and fractions of these molecules can be deposited onto substrates using CVD. Following its deposition onto a substrate, the alkylated silsesquioxane layer is cured, producing a low k dielectric layer or film.

In a first aspect, the present invention provides a composition comprising a vaporized material having the formula $[R—SiO_{1.5}]_x[H—SiO_{1.5}]_y$, wherein x+y=n, n is an integer between 2 and 30, x is an integer between 1 and n and y is a whole number between 0 and n. R is a $C_1$ to $C_{100}$ alkyl group.

In a second aspect, the present invention provides a method of forming a low k dielectric film. The method comprises vaporizing and depositing on a substrate a material having the formula $[R—SiO_{1.5}]_x[H—SiO_{1.5}]_y$, wherein x+y=n, n is an integer between 2 and 30, x is an integer between 1 and n and y is a whole number between 0 and n. R is a $C_1$ to $C_{100}$ alkyl group.

In a third aspect, the invention provides a low k dielectric film comprising a material having the formula $[H_aSiO_b]_c[(R^1)_aSiO_b]_d[(R^2)_aSiO_b]_n$. In this formula $R^1$ and $R^2$ are members independently selected from $C_1$ to $C_{100}$ alkyl groups; a is less than or equal to 1; b is greater than or equal to 1.5; and c, d and n are members independently selected from the group consisting of the integers greater than 10.

In a fourth aspect, the present invention provides an object comprising a low k dielectric film comprising a material having the formula $[H_aSiO_b]_c[(R^1)_aSiO_b]_d[(R^2)_aSiO_b]_n$. In this formula $R_1$ and $R_2$ are members independently selected from $C_1$ to $C_{100}$ alkyl groups; a is less than or equal to 1; b is greater than or equal to 1.5; and c, d and n are members independently selected from the group consisting of the integers greater than 10.

These and other aspects and advantages of the present invention will be apparent from the detailed description that follows.

DETAILED DESCRIPTION OF THE INVENTION AND THE PREFERRED EMBODIMENTS

Abbreviations and Definitions

Figure 1:
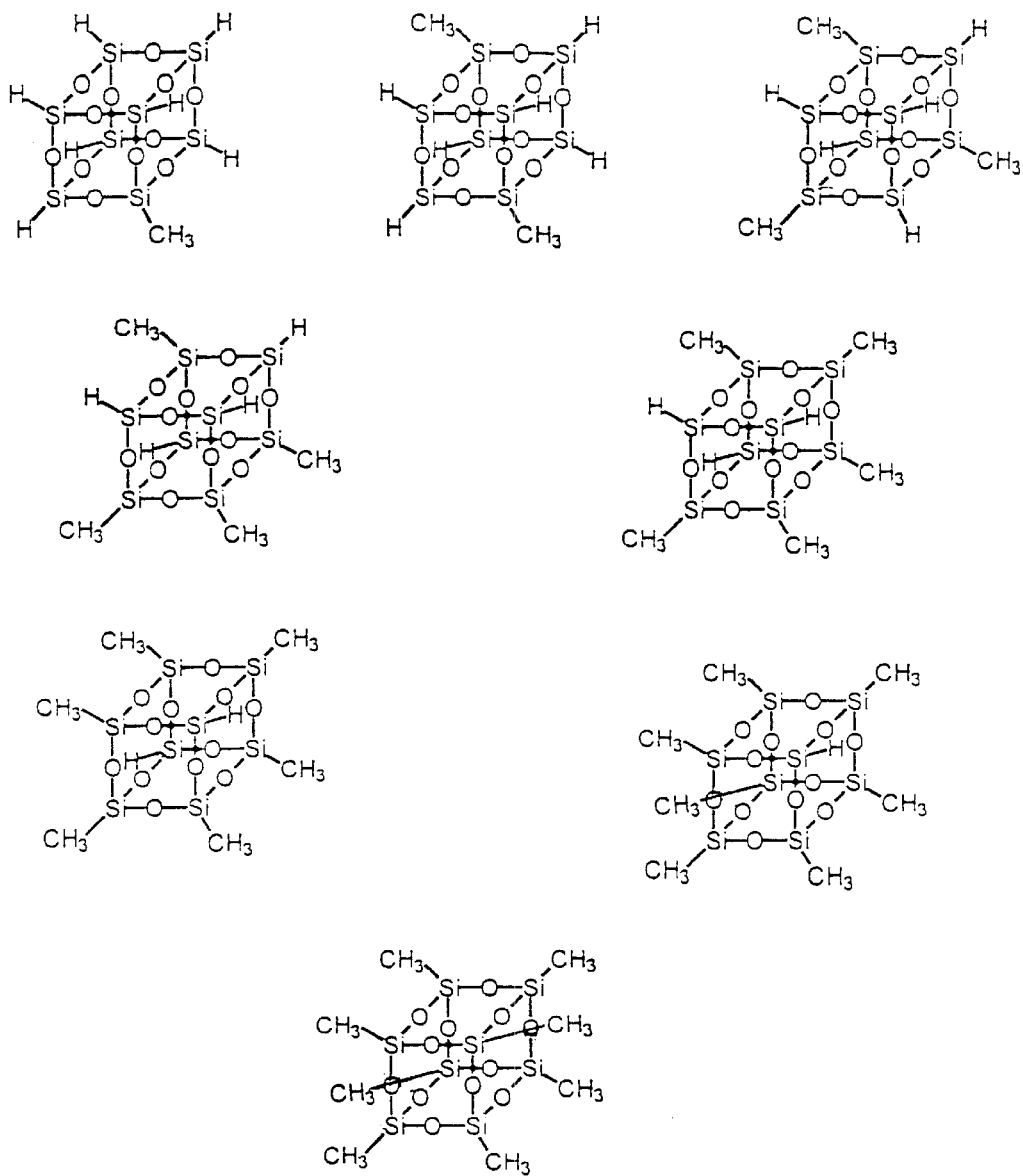
FIG. 1 is a group of three-dimensional structural formulae for the methyl-substituted silsesquioxanes of the invention.
Figure 2:
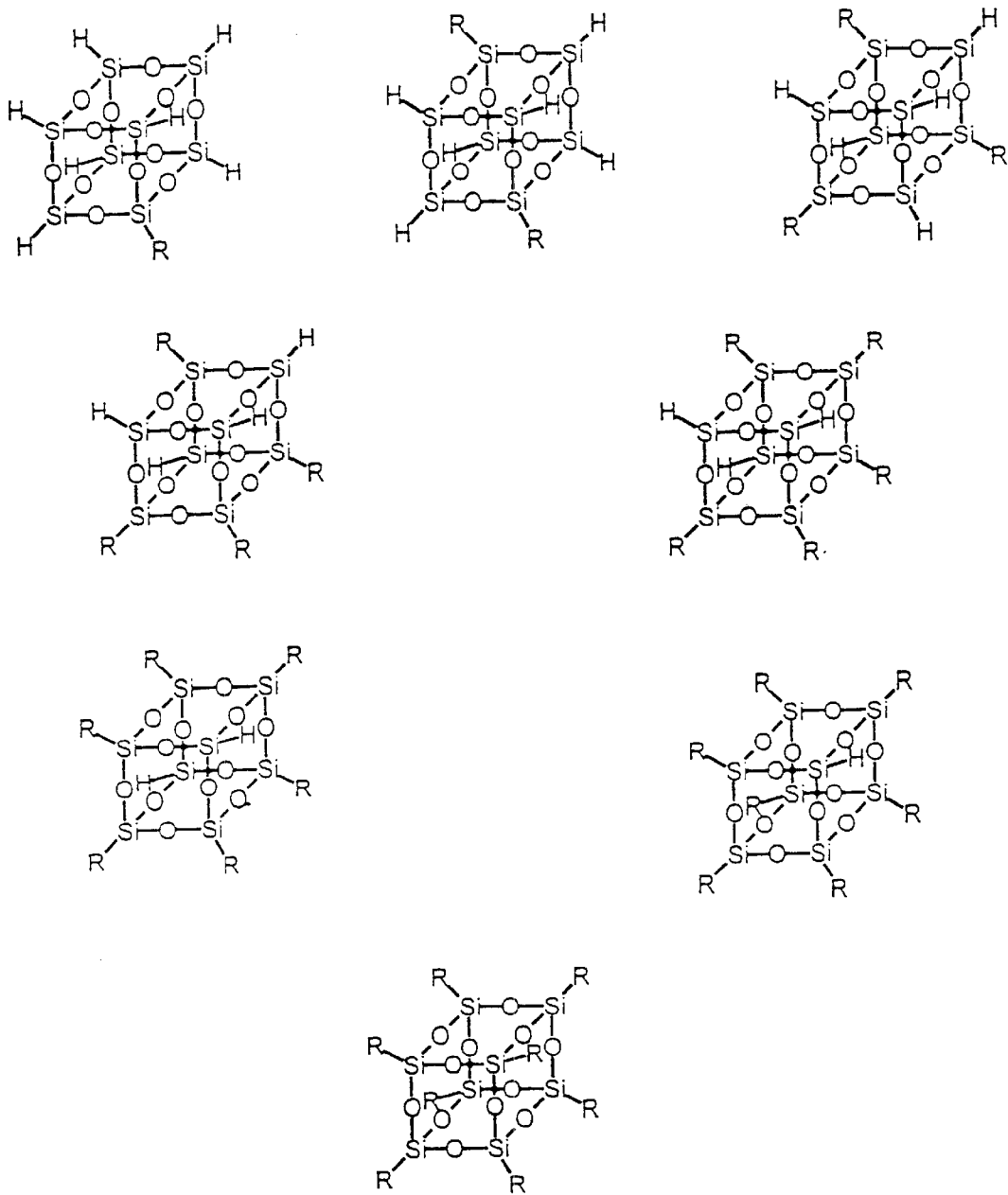
FIG. 2 is a group of three-dimensional structural formulae for the alkyl-substituted silsesquioxanes of the invention.
Figure 3:
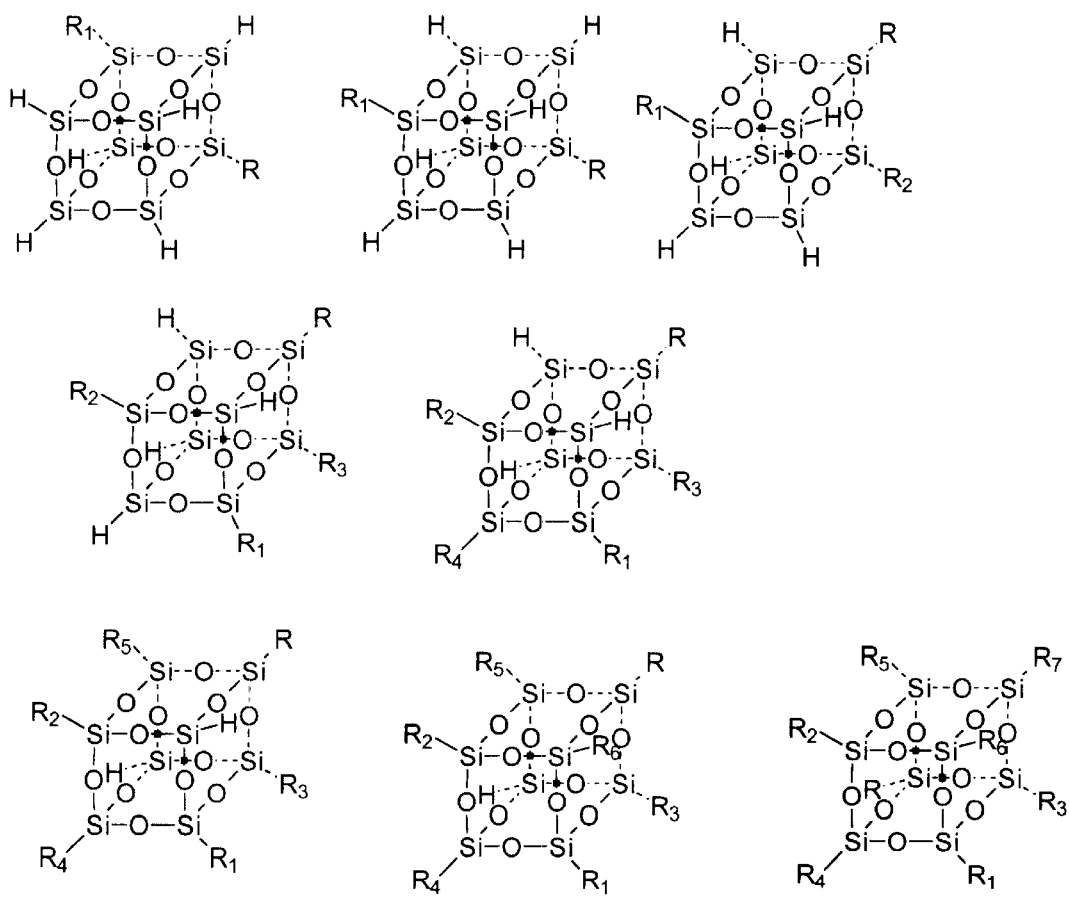
FIG. 3 is a group of three-dimensional structural formulae for the alkyl-substituted silsesquioxanes of the invention, wherein each R group is the same as, or different from the other R groups.

"CVD," as used herein, refers to "chemical vapor deposition."

"AHSQ," as used herein refers to "alkylated hydrogen silsesquioxanes."

"ASQ," as used herein, refers to "alkylated silsesquioxanes."

"ASX," as used herein, refers to "alkylated fluorinated siloxanes."

"AHSX," as used herein, refers to "alkylated fluorinated hydrogen siloxanes."

The terms "alkylated silsesquioxanes" and "alkylated hydrogen silsesquioxanes" are used herein to describe various silane resins having the formula $[R-SiO_{1.5}]_x[(H-SiO_{1.5}]_y$, wherein x+y=n, n is an integer between 2 and 30, x is an integer between 1 and n and y is a whole number between 0 and n. R is a $C_1$ to $C_{100}$ alkyl group. "Alkylated silsesquioxanes" refer to silsesquioxanes in which substantially every silicon atom has an alkyl group attached thereto. "Alkylated hydrogen silsesquioxanes" refer to silsesquioxanes having a mixture of alkylated silicon atoms and silicon atoms bearing hydrogen. "Silsesquioxane" is used generically herein to refer to both of the above-described species.

Though not explicitly represented by this structure, these resins may contain a small number of silicon atoms which have either 0 or 2 hydrogen atoms or alkyl groups attached thereto due to various factors involved in their formation or handling.

The terms "alkylated siloxane film" and "alkylated hydrogen siloxane film" refer to films resulting from curing the deposited silsesquioxane. The films have the generic formula $[H_aSiO_b]_c[(R^1)_aSiO_b]_d[(R^2)_aSiO_b]_n$. In this formula $R^1$ and $R^2$ are members independently selected from $C_1$ to $C_{100}$ alkyl groups; a is less than or equal to 1; b is greater than or equal to 1.5; and c, d and n are members independently selected from the group consisting of the integers greater than 10.

"Low k," as used herein, refers to a dielectric constant that is lower than that of an $SiO_2$ film.

Introduction

The present invention is based on the discovery that fractions of fully alkylated silsesquioxanes and alkylated hydrogen silsesquioxanes can be used to form coatings on various substrates. The compounds are deposited onto a substrate, such as a semiconductor wafer by CVD. Following their deposition, the film is cured to produce a low k dielectric film. The films produced by the techniques described herein are valuable as protective and dielectric layers on substrates such as electronic devices.

The invention provides methods of forming low k dielectric films. Additionally, there is provided an array of low k films and compounds useful for forming these films.

The Compounds

In a first aspect, the present invention provides a composition comprising a vaporized material having the formula $[R-SiO_{1.5}]_x[H-SiO_{1.5}]_y$, wherein x+y=n, n is an integer between 2 and 30, x is an integer between 1 and n and y is a whole number between 0 and n. R is a $C_1$ to $C_{100}$ alkyl group. Presently preferred mole % carbon content is from about 20% to about 90%, more preferably from about 40% to about 80%.

The silsesquioxanes of the invention are alkyl-substituted molecules that, at higher values of n, exist as cage "T-n" molecules (e.g., T-8, T-10, etc.). In a preferred embodiment, n is an integer with a value from 2 to 16. In a further preferred embodiment, n is an integer with a value from 8 to 12.

These compounds can be synthesized by a number of art-recognized methods. For example ASQ can be synthesized by the hydrolysis and condensation of $R-Si-X_3$, wherein R is methyl or a $C_2-C_{100}$ alkyl group. In a preferred embodiment, the alkyl group is a $C_1$ to $C_{20}$ alkyl group. In another preferred embodiment, the alkyl group is a $C_1$ to $C_{16}$ alkyl group. In yet another preferred embodiment, the alkyl group is $C_1$ to $C_6$. The alkyl groups can be either straight- or branched chain alkyl groups.

In the formula provided above, X represents a species that is eliminated during hydrolysis. Currently, preferred X groups are halogens, alkoxy groups and aryloxy groups, more preferably halogens and even more preferably Cl.

The hydrolysis/condensation reactions preferably result in a fully condensed ASQ or AHSQ or the hydrolysis and/or condensation may be interrupted at an intermediate point such that partial hydrolysates (containing Si—OR, Si—Cl, etc.) and/or partial condensates (containing SiOH groups) are formed. See, for example, Olsson, *Arkiv. Keini.* 13: 367–78 (1958); Barry et al., *J. Am. Chem. Soc.* 77: 4248–52 (1955); and Dittmar et al., *J. Organomet. Chem.* 489: 185–194 (1995). In a preferred embodiment, the reaction produces substantially fully condensed silsesquioxanes.

ASQ and AHSQ having alkyl groups of more than one structure or composition substituted onto a single silicon framework are prepared by cohydrolysis of organotrihalosilanes or organotrialkoxysilanes where the components of the cohydrolysis reaction bear different alkyl groups at the silicon atom. For example, the cohydrolysis of $CH_3SiCl_3$ and $CH_3CH_2SiCl_3$ will provide a silsesquioxane having both methyl and ethyl functionality on the silicon atoms of the silsesquioxane. See, for example, Hendan et al., *J. Organomet. Chem.* 483: 33–8 (1994). The alkyl content of the ASQ and AHSQ can be controlled by manipulation of the stoichiometry of the hydrolysis reaction.

The hydrolysis/condensation reactions can be performed in a number of different reaction milieus and the choice of appropriate reaction conditions is well within the abilities of those of skill in the art. The hydrolysis and condensation polymerization is generally carried out using conventional equipment, by the addition of the organosilane monomer (or both monomers in the case of copolymerization) to an aqueous medium. The aqueous medium can be simply water or it can be an aqueous alcohol. Additionally, catalysts such as organic and/or inorganic acids or bases can be added to the reaction mixture. For example, when silane alkoxides are utilized as precursors for the silsesquioxane, it is often desirable to use an acidic catalyst (e.g., HCl) to facilitate the reaction. Moreover, when silane halides are utilized as precursors, a basic reaction environment often facilitates the reaction. See, for example, Wacker et al., U.S. Patent No. 5,047,492, Sep. 10, 1991.

The silane monomers (e.g., $CH_3SiCl_3$, $HSiCl_3$, etc.) can be added neat to the hydrolysis mixture or they can be first solubilized in a solvent (e.g., hexanes, methylene chloride, methanol, etc.). The monomer(s) is preferably added at a measured rate to the hydrolysis medium to obtain more precise control of the hydrolysis and condensation. In a preferred embodiment, wherein two or more monomers are utilized, a mixture of the monomers is formed and then this mixture is added to the hydrolysis mixture.

Additional control of the hydrolysis and condensation polymerization reactions can also be obtained though adjustment of the temperature of the hydrolysis reaction medium, by maintaining the reaction temperature in the range of about 0° C. to about 50° C. Preferably, the temperature of the hydrolysis reaction medium is maintained at a temperature from about 0° C. to about 5° C.

In yet another embodiment, alkylated silsesquioxanes are prepared by the cross-metathesis of alkenes with readily available vinyl-substituted silsesquioxanes. This reaction is quite general and is unhindered by self-metathesis of the vinyl-substituted silsesquioxanes. See, for example, Feher et al., *Chem. Commun.* 13: 1185–1186 (1997).

In a still further embodiment, the ASQ or AHSQ molecules are synthesized by hydrosilation of a precursor hydrogen silsesquioxane or AHSQ. This method affords access to ASQ molecules and AHSQ molecules (mono-, di-, tri-substituted, etc.), depending on the stoichiometry of the reaction between the silsesquioxane and the incoming hydrosilating species. In a preferred embodiment, the silsesquioxane cage is hydrosilated with an alkene. Hydrosilation reactions of the silsesquioxanes are typically carried out under catalytic conditions. In a presently preferred embodiment, the catalyst is a platinum catalyst, such as a chloroplatinic acid. See, for example, Bolln et al., *Chem. Mater.* 9: 1475–1479 (1997); Bassindale et al., In, *Tailor-Made Silicon-Oxygen Compounds*; pp.171–176, Eds. Corriu et al., Vieweg, Wiesbaden, Germany (1995); Calzaferri et al., *Helv. Chim. Acta* 74: 1278–1280 (1991); Herren et al. *Helv. Chim. Acta* 74: 24–6 (1991); and Dittmar et al., *J. Organomet. Chem.* 489: 185–194 (1995).

Certain of the starting hydrogen silsesquioxane used in the hydrosilation reaction are commercially available. For example, the T-8 cage is commercially available (Aldrich Chemical Co., Dow Corning, Hitachi). Moreover, various methods for the production of hydrogen silsesquioxanes have been developed. For instance, Collins et al. in U.S. Pat. No. 3,615,272, which is incorporated herein by reference, describe a process of forming nearly fully condensed hydrogen silsesquioxane (which may contain up to 100–300 ppm silanol) comprising hydrolyzing trichlorosilane in a benzenesulfonic acid hydrate hydrolysis medium and then washing the resulting product with water or aqueous sulfuric acid. Similarly, Bank et al. in U.S. Pat. No. 5,010,159, Apr. 23, 1991, disclose methods of forming hydrogen silsesquioxanes comprising hydrolyzing hydridosilanes in an arylsulfonic acid hydrate hydrolysis medium to form a resin which is then contacted with a neutralizing agent. A preferred embodiment of this latter process uses an acid to silane ratio of about 6/1.

Higher order silsesquioxane cages (e.g., T-10, -12, etc.) can be prepared by, for example, partial rearrangement of octasilsesquioxane cages. These rearrangement reactions are catalyzed by compounds such as sodium acetate, sodium cyanate, sodium sulfite, sodium hydroxide and potassium carbonate. The reactions are generally carried out in an organic solvent, preferably acetone. See, for example, Rikowski et al., *Polyhedron* 16: 3357–3361 (1997).

Recovery of the silsesquioxane reaction product from the aqueous reaction medium may be carried out using conventional techniques (e.g., solvent extraction with organic solvents that solubilize the reaction product but are immiscible with the aqueous reaction medium), salting-out of the silsesquioxane reaction product, and the like. The silsesquioxane reaction product can then be recovered by filtration or evaporation of the extract solvent as applicable.

The compounds can be purified by techniques common in the art of organic chemistry including chromatography (e.g., gel permeation, silica gel, reverse-phase, HPLC, FPLC, etc.), crystallization, precipitation, fractionation, ultrafiltration, dialysis and the like. In a presently preferred embodiment, the desired material is purified by fractionation and precipitation.

Art-recognized analytical methods can be used to characterize the compounds. Useful methods include spectroscopic techniques (e.g., $^1$H, $^{13}$C, $^{19}$F NMR, infrared), mass spectrometry, gel permeation chromatography against a molecular weight standard, elemental analysis, melting point determination and the like. In a preferred embodiment, the compounds are characterized by a protocol involving each of these techniques.

In an exemplary embodiment, a trichlorosilane (~25 g) is added drop-wise with stirring to distilled water (~250 mL) and a non-polar solvent (e.g., hexanes, toluene) at a temperature of about 0° C. Upon completion of the addition of the silane, the reaction is allowed to stir for between 10 minutes and 24 hours. If a precipitate forms in the aqueous mixture, this mixture can be clarified by filtration or centrifugation. An organic solvent such as hexane is then added to the aqueous reaction medium. The resulting mixture is stirred for a time sufficient to allow the extraction of the reaction product from the aqueous medium. The organic layer is removed from the aqueous layer and the aqueous phase is extracted further with three washings of the organic solvent (~3×100 mL). The hexane washings are combined with the original organic phase extract, and the combined organic phase solution is dried by contacting it with sodium sulfate, and thereafter it is filtered. After evaporation of the solvent from the organic phase extract, the recovered reaction product is dried under high vacuum to yield the desired product. The product can be characterized by $^1$H and $^{29}$Si NMR, mass spectrometry and elemental analysis. The molecular weight of the product is determined by GPC relative to a standard, such as a polystyrene calibration standard.

Low k dielectric films with desirable physical properties can also be prepared using copolymers of alkylsilanes copolymerized with trichlorosilane. In an exemplary embodiment, an AHSQ molecule is prepared by the hydrolysis condensation method. In this embodiment, the alkyl content of the final product is controlled by the stoichiometric ratio of the alkyl silane to trichlorosilane. Thus, to prepare a product that has an average of 3:1 methyl to hydrogen, methyltrichlorosilane (3 moles) and trichlorosilane (1 mole) are combined, and the combined components are added dropwise with stirring to distilled water (~250 mL) and a non-polar solvent at a temperature of about 0° C. After stirring for a period of from about 10 minutes to about 24 hours, an organic solvent such as hexane (~250 mL) is added to the aqueous reaction medium to extract the reaction product from the aqueous medium, and the reaction mixture is stirred for ten minutes. The work up of the reaction mixture and the characterization of the product are substantially similar to that described for the homopolymer above.

In a preferred embodiment, the ASQ or AHSQ polymer is deposited by vapor deposition, however, certain of the above-described reactions can lead to the production of ASQ and AHSQ polymers that have a molecular weight that is too high to allow these polymers to be vaporized in useful quantities. Although, the volatile fraction can be vaporized and used to form a film, leaving behind the higher molecular weight fraction, in a preferred embodiment, the high molecular weight molecules are removed from the more volatile components of the product mixture prior to using these compounds for vapor deposition.

Separation of the high and low molecular weight fractions can be accomplished by a number of means including, for example, gel permeation chromatography, high performance liquid chromatography (HPLC), ultrafiltration, fractional crystallization and solvent fractionation. Each of these methods is well known in the art and it is within the abilities of one of skill in the art to devise an appropriate purification protocol for a particular mixture without undue experimentation. When other deposition methods are utilized, the volatility of the film precursor is less of a concern.

In a preferred embodiment, using vapor deposition, the product mixture is fractionated to obtain the low molecular weight species that can be volatilized in the deposition process of this invention. Any conventional technique for fractionating the polymer can be used herein. Particularly preferred, however, is the use of a variety of fluids at, near or above their critical point. This process is described in Hanneman et al., U.S. Pat. No. 5,118,530, Jun. 2, 1992. The process described therein comprises (1) contacting the H-resin with a fluid at, near or above its critical point for a time sufficient to dissolve a fraction of the polymer; (2) separating the fluid containing the fraction from the residual polymer; and (3) recovering the desired fraction.

Specifically, the fractionation method involves charging an extraction vessel with a silsesquioxane product mixture and then passing an extraction fluid through the vessel. The extraction fluid and its solubility characteristics are controlled so that only the desired molecular weight fractions of silsesquioxane are dissolved. The solution with the desired fractions of silsesquioxane is then removed from the vessel leaving those silsesquioxane fractions not soluble in the fluid as well as any other insoluble materials such as gels or contaminants. The desired silsesquioxane fraction is then recovered from the solution by altering the solubility characteristics of the solvent and, thereby, precipitating out the desired fraction. These precipitates can then be collected by a process such as filtration or centrifugation.

The extraction fluid used in this process includes any compound which, when at, near or above its critical point, will dissolve the fraction of silsesquioxane desired and not dissolve the remaining fractions. Additional consideration, however, is usually given to the critical temperature and pressure of the solvent compound so that unreasonable measures are not necessary to reach the appropriate point. Examples of specific compounds that are functional include, but are not limited to, carbon dioxide and most low molecular weight hydrocarbons such as ethane or propane. Additional methods of fractionation are disclosed in Katsutoshi et al., U.S. Pat. No. 5,486,546, Jan. 23, 1996.

By such methods, one can recover the desired fraction of an AHSQ or ASQ. Other equivalent methods, however, which result in obtaining the fractions described herein are also contemplated. For instance, methods such as solution fractionation or sublimation function herein (See, for example, Olsson et al., *Arkiv. Kemi* 13: 367–78 (1958)).

When a vapor deposition method is used, the preferred fraction of silsesquioxane used in the process of this invention is one that can be volatilized under moderate temperature and/or vacuum conditions. Generally, such fractions are those in which at least about 75% of the species have a molecular weight less than about 3000. Preferred herein, however, are those fractions in which at least about 75% of the species have a molecular weight less than about 1800, with those fractions in which at least about 75% of the species have a molecular weight between about 400 and 1600 being particularly preferred. In preferred embodiments, this molecular weight range will correspond to compounds that are T-2 to T-30 cages. For vapor deposition, preferred species correspond to compounds that are T-2 to T-16, and for spin on applications, T-12 to T-30.

Additionally, it is contemplated that mixtures of silsesquioxanes containing components that are not easily vaporized can be used herein as the source of silsesquioxane vapor. Volatilization of such mixtures, however, can leave a residue comprising nonvolatile species. This residue does not constitute an impediment to the use of silsesquioxane mixtures containing compounds having a broad range of molecular weights.

Chemical Vapor Deposition (CVD)

Any deposition method known in the art can be used to produce a film using one or more compounds of the invention. Deposition techniques of general applicability include, for example, spraying (e.g., nebulizer under vacuum), spin-on, dip-coating, sputtering, CVD, and the like. Other coating methods will be apparent to those of skill in the art.

As the use of CVD is presently preferred, in a second aspect, the invention provides a method of forming a low k dielectric film. The method comprises vaporizing and depositing on a substrate a material having the formula $[R-SiO_{1.5}]_x[H-SiO_{1.5}]_y$, wherein x+y=n, n is an integer between 2 and 30, x is an integer between 1 and n and y is a whole number between 0 and n. R is a $C_1$ to $C_{100}$ alkyl group.

In an exemplary embodiment, the desired fraction of silsesquioxane is obtained, and it is placed into a CVD apparatus, vaporized and introduced into a deposition chamber containing the substrate to be coated. Vaporization can be accomplished by heating the silsesquioxane sample above its vaporization point, by the use of vacuum, or by a combination of the above. Generally, vaporization is accomplished at temperatures in the range of 50° C.–300° C. under atmospheric pressure or at lower temperature (near room temperature) under vacuum.

The amount of silsesquioxane vapor used in the process of this invention is that which is sufficient to deposit the desired coating. This can vary over a wide range depending on factors such as the desired coating thickness, the area to be coated, etc. In addition, the vapor may be used at nearly any concentration desired. If dilute vapor is to be used, it may be combined with nearly any compatible gas such as air, argon or helium.

The process of this invention can be used to deposit desirable coatings in a wide variety of thicknesses. For instance, coatings in the range of from about a monolayer to greater than about 2–3 microns are possible. Greater film thicknesses are possible where end use applications warrant such thicker films. Multiple coating applications of layered thin films are preferred for preparing ceramic films that are 4 microns or more in thickness, to minimize stress cracking.

These coatings may also cover, or be covered by other coatings such as $SiO_2$ coatings, $SiO_2$/modifying ceramic oxide layers, silicon containing coatings, silicon carbon containing coatings, silicon nitrogen containing coatings, silicon nitrogen carbon containing coatings, silicon oxygen nitrogen containing coatings, and/or diamond like carbon coatings. Such coatings and their mechanism of deposition are known in the art. For example, many are taught in Haluska, U.S. Pat. No. 4,973,526, Nov. 27, 1990.

The formation of the films of the invention is accomplished by a large variety of techniques, which can conceptually be divided into two groups: (1) film growth by interaction of a vapor-deposited species with the substrate; and (2) film formation by deposition without causing changes to the substrate or film material. See, for example, Bunshah et al., *Deposition Technologies for Films and Coatings*, Noyes, Park Ridge, N.J., 1983; and Vossen et al., *Thin Film Processes*, Academic Press, New York, N.Y., 1978.

The second group is most relevant to the present invention and it includes another three subclasses of deposition: (a) chemical vapor deposition, or CVD, in which solid films are formed on a substrate by the chemical reaction of vapor phase chemicals that contain the required constituents; (b) physical vapor deposition, or PVD, in which the species of the thin film are physically dislodged from a source to form a vapor which is transported across a reduced pressure region to the substrate, where it condenses to form the thin film; and (c) coating of the substrate with a liquid, which is then dried to form the solid thin film. When a CVD process is used to form single-crystal thin films, the process is termed epitaxy. The formation of thin films by PVD includes the processes of sputtering and evaporation.

There are currently three major types of chemical vapor deposition (CVD) processes, atmospheric pressure CVD (APCVD), low pressure (LPCVD) and plasma enhanced CVD (PECVD). Each of these methods has advantages and disadvantages. The choice of an appropriate CVD method and device for a particular application is well within the abilities of those of skill in the art.

Atmospheric pressure CVD (APCVD) devices operate in a mass transport limited reaction mode at temperatures of approximately 400° C. In mass-transport limited deposition, temperature control of the deposition chamber is less critical than in other methods: mass transport processes are only weakly dependent on temperature. As the arrival rate of the reactants is directly proportional to their concentration in the bulk gas, maintaining a homogeneous concentration of reactants in the bulk gas adjacent to the wafers is critical. Thus, to insure films of uniform thickness across a wafer, reactors that are operated in the mass transport limited regime must be designed so that all wafer surfaces are supplied with an equal flux of reactant. The most widely used APCVD reactor designs provide a uniform supply of reactants by horizontally positioning the wafers and moving them under a gas stream.

In contrast to APCVD reactors, low pressure CVD (LPCVD) reactors operate in a reaction rate-limited mode. In processes that are run under reaction rate-limited conditions, the temperature of the process is an important parameter. To maintain a uniform deposition rate throughout a reactor, the reactor temperature must be homogeneous throughout the reactor and at all wafer surfaces. Under reaction rate-limited conditions the rate at which the deposited species arrive at the surface is not as critical as constant temperature. Thus, LPCVD reactors do not have to be designed to supply an invariant flux of reactants to all locations of a wafer surface.

Under the low pressure of an LPCVD reactor, for example, operating at medium vacuum (30–250 Pa or 0.25–2.0 torr) and higher temperatures (550–600° C.), the diffusivity of the deposited species is increased by a factor of approximately 1000 over the diffusivity at atmospheric pressure. The increased diffusivity is partially offset by the fact that the distance across which the reactants must diffuse increases by less than the square root of the pressure. The net effect is that there is more than an order of magnitude increase in the transport of reactants to the substrate surface and by-products away from the substrate surface.

LPCVD reactors are designed in two primary configurations: (a) horizontal tube reactors; and (b) vertical flow isothermal reactors. Horizontal tube, hot wall reactors are the most widely used LPCVD reactors in VLSI processing. They are employed for depositing poly-Si, silicon nitride, and undoped and doped $SiO_2$ films. They find such broad applicability primarily because of their superior economy, throughput, uniformity, and ability to accommodate large diameter (e.g., 150 mm) wafers.

The vertical flow isothermal LPCVD reactor further extends the distributed gas feed technique, so that each wafer receives an identical supply of fresh reactants. Wafers are again stacked side by side, but are placed in perforated-quartz cages. The cages are positioned beneath long, perforated, quartz reaction-gas injector tubes, one tube for each reactant gas. Gas flows vertically from the injector tubes, through the cage perforations, past the wafers, parallel to the wafer surface and into exhaust slots below the cage. The size, number, and location of cage perforations are used to control the flow of reactant gases to the wafer surfaces. By properly optimizing cage perforation design, each wafer can be supplied with identical quantities of fresh reactants from the vertically adjacent injector tubes. Thus, this design can avoid the wafer-to-wafer reactant depletion effects of the end-feed tube reactors, requires no temperature ramping, produces highly uniform depositions, and reportedly achieves low particulate contamination.

The third major CVD deposition method is plasma enhanced CVD (PECVD). This method is categorized not only by pressure regime, but also by its method of energy input. Rather than relying solely on thermal energy to initiate and sustain chemical reactions, PECVD uses an rf-induced glow discharge to transfer energy into the reactant gases, allowing the substrate to remain at a lower temperature than in APCVD or LPCVD processes. Lower substrate temperature is the major advantage of PECVD, providing film deposition on substrates not having sufficient thermal stability to accept coating by other methods. PECVD can also enhance deposition rates over those achieved using thermal reactions. Moreover, PECVD can produce films having unique compositions and properties. Desirable properties such as good adhesion, low pinhole density, good step coverage, adequate electrical properties, and compatibility with fine-line pattern transfer processes, have led to application of these films in VLSI.

PECVD requires control and optimization of several deposition parameters, including rf power density, frequency, and duty cycle. The deposition process is dependent in a complex and interdependent way on these parameters, as well as on the usual parameters of gas composition, flow rates, temperature, and pressure. Furthermore, as with LPCVD, the PECVD method is surface reaction limited, and adequate substrate temperature control is thus necessary to ensure uniform film thickness.

CVD systems usually contain the following components: (a) gas sources; (b) gas feed lines; (c) mass-flow controllers for metering the gases into the system; (d) a reaction chamber or reactor; (e) a method for heating the wafers onto which the film is to be deposited, and in some types of systems, for adding additional energy by other means; and (f) temperature sensors. LPCVD and PECVD systems also contain pumps for establishing the reduced pressure and exhausting the gases from the chamber.

In a preferred embodiment, the films of the invention are produced using CVD with a heated substrate.

Curing

In a third aspect, the invention provides a low k dielectric film comprising a material having the formula $[H_aSiO_b]_c$ $[(R^1)_aSiO_b]_d[(R^2)_aSiO_b]_n$. In this formula $R^1$ and $R^2$ are members independently selected from $C_1$ to $C_{100}$ alkyl groups; a is less than or equal to 1; b is greater than or equal to 1.5; and c, d and n are members independently selected from the group consisting of the integers greater than 10, more preferably greater than 100, greater than 1000, greater than 10,000 or greater than 100,000.

In a preferred embodiment, the precursor for this film is a silsesquioxane having the formula $[R—SiO_{1.5}]_x[H—SiO_{1.5}]_y$, wherein x+y=n, n is an integer between 2 and 30, x is an integer between 1 and n, and y is a whole number between 0 and n. R is a $C_1$ to $C_{100}$ alkyl group. In a further preferred embodiment, R is a $C_2$ to $C_{80}$ alkyl group, preferably a $C_4$ to $C_{40}$ alkyl group, and more preferably a $C_6$ to $C_{20}$ alkyl group. This film is formed by curing the film of silsesquioxane molecule deposited onto the substrate. When the alkyl group is a methyl group, the cured film contains methyl moieties. In contrast, when the alkyl group is a higher alkyl, $C_n$ (n=2–100), the process of curing results in the extrusion of an alkene moiety having n–1 carbon atoms. The extrusion of the alkene moiety from the curing film creates a pore in the film. The size of this pore can be manipulated by the size of the alkyl group of the film precursor. Thus, films of varying porosity and, therefore, varying dielectric constants can be formed using the methods of the invention.

Thus, in a fourth aspect, the present invention provides a method for preparing a porous low k dielectric film having a preselected degree of porosity. The film has the formula $[H_aSiO_b]_c[(R^1)_aSiO_b]_d[(R^2)_aSiO_b]_n$. In this formula $R^1$ and $R^2$ are members independently selected from $C_1$ to $C_{100}$ alkyl groups; a is less than or equal to 1; b is greater than or equal to 1.5; and c, d and n are members independently selected from the group consisting of the integers greater than 10. The method comprises depositing a film precursor comprising a material having the formula $[R—SiO_{1.5}]_x[H—SiO_{1.5}]_y$, wherein x+y=n, n is an integer between 2 and 30, x is an integer between 1 and n, y is a number between 0 and n, R is a $C_1$ to $C_{100}$ alkyl group and the R group is of a size sufficient to provide the preselected degree of porosity. The deposited film precursor is then cured to produce the porous low k film.

As used herein, "degree of porosity" refers to both the size of the pores in the film and the number of pores per unit area. The effect of any given R group on the degree of film porosity is easily determined. Following a simple experimental protocol, one of skill can select a film precursor or series of film precursors that provide films with a preselected degree of porosity without undue experimentation. In an exemplary experimental protocol, the size of the pores is varied over a series of films by the orderly variation of the size of the R group on the film precursor. To a first approximation, an R group is selected, and the resulting pore size is estimated, on the basis of the van der Waals radius of the extruded alkene. The van der Waals radius provides a useful parameter for estimating the size of the pore resulting from the extrusion of the alkene group. To arrive at a desired level of porosity, a series of films, having the same number of alkyl substituents, but varying in the size of the alkyl substituents is prepared and cured to produce the corresponding porous films. The porosity of the films is then assessed by, inter alia, measuring their density. In another embodiment, the number of pores in a film is manipulated by varying the number of alkyl substituents on the film precursor. The following discussion is generally applicable to the two aspects of the invention discussed immediately above. Prior to initiating the curing process, a film reflow process can be performed to smooth the surface of the film. After coating, silsesquioxane film reflow can be effected by raising the temperature of the substrate to a temperature between 120° C. and 200° C., typically for about 5 minutes. This step may be done in air, or in the curing ambient, at a convenient pressure (typically atmospheric). Alternately, this step can be combined with the following curing step under most curing conditions applicable to an ILD or PO deposition.

Prior art silsesquioxane-derived films have been cured in various ambients, resulting in widely varying properties. These ambients include air, ammonia, nitrogen, nitrogen/argon, and hydrogen/nitrogen. Generally, temperatures of about 400° C. and curing times of about 30 minutes to an hour are also taught in the prior art. In particular, it has been found that curing in air produces a predominantly Si—O film, curing in ammonia produces a silicon oxynitride type film, and curing in inert or reducing atmospheres results in films which retain some portion of the Si—H bonding inherent in uncured hydrogen silsesquioxane.

The present invention is comprehended for use in silsesquioxane films dried and cured in all ambients, including reducing or inert ambients other than those discussed herein. Even films that are carefully cured under non-oxidizing conditions may eventually become exposed to moisture and/or oxygen, either during further processing of the device, during packaging, or in use. The invention is also comprehended for use with deposition methods that use trace amounts of a group VIII catalyst, such as $Pt(acac)_2$, to further HSQ film curing.

The formation of a silsesquioxane thin film is effected by processing the coated substrate, via treatment at moderately elevated temperatures or with UV irradiation, or an incident electron beam to convert the silsesquioxane molecule composition into a silsesquioxane thin film. This crosslinking conversion is carried out in a moisture-containing atmosphere containing at least about 0.5% relative humidity and preferably containing from about 15% relative humidity to about 100% relative humidity. The specified level of moisture may be present in the atmosphere during the entire processing procedure for forming the ceramic thin film or, alternatively, can be present during only a portion of the procedure.

In addition to the moisture-containing atmosphere, and inert gases such as nitrogen, argon, helium or the like may be present or reactive gases such as air, oxygen, hydrogen chloride, ammonia and the like may be present.

In one embodiment of this invention, the conversion of the silsesquioxane molecule on the coated substrate is accomplished via thermal processing, by heating the coated substrate. The temperature employed during the heating to form the thin film is moderate, preferably being at least about 100° C., more preferably at least about 150° C. Extremely high temperatures, which are often deleterious to other materials present on the substrate, e.g., particularly metallized electronic substrates, are generally unnecessary. Heating temperatures in the range of about 150° C. to about 700° C. are preferable, with temperatures in the range of about 200° C. to about 500° C. being more preferred. The exact temperature will depend on factors such as the particular substituted organosilsesquioxane molecule utilized, the composition of the atmosphere (including relative humidity), heating time, coating thickness and coating composition components. The selection of appropriate conditions is well within the abilities of those of skill in the art.

Heating is generally conducted for a time sufficient to form the desired thin film. The heating period typically is in the range of up to about 6 hours. Heating times of less than about 2 hours, e.g., about 0.1 to about 2 hours, are preferred. The heating procedure is generally conducted at ambient pressure (i.e., atmospheric pressure), but subatmospheric pressure or a partial vacuum or superatmospheric pressures may also be employed. Any method of heating, such as the use of a convection oven, rapid thermal processing, hot plate, or radiant or microwave energy is generally functional. The rate of heating, moreover, is also not critical, but it is most practical and preferred to heat as rapidly as possible.

In an alternative embodiment of this invention, the formation of a silsesqujoxane thin film is accomplished by subjecting the coated substrate to ultraviolet (UV) irradiation or an electron beam. Exposure of the coated substrate to such irradiation has been found to effect the desired crosslinking conversion of the silsesquioxane molecule in the coated substrate. The irradiation treatment is ordinarily carried out without subjecting the coated substrate to the elevated temperatures used in the thermal processing, but combinations of the irradiation and thermal processing treatments could be employed, if desired.

The silsesquioxane thin films formed using irradiation-based processing are generally characterized as having higher $SiO_2$ contents than typically result from thermal processing under otherwise identical coating conditions. An advantage of the use of irradiation-based processing is that patterned films may be generated on a substrate by the selective focusing of the radiation.

Characterization

Although the properties of a bulk material are well characterized, the same material in its thin film form can have properties that are substantially different from those of the bulk material. One reason is that thin film properties are strongly influenced by surface properties, while in bulk materials this is not the case. The thin film, by its very definition, has a substantially higher surface-to-volume ratio than does a bulk material. The structure of thin films, and their method of preparation also play a vital role in determining the film properties.

There exists an array of art-recognized techniques for characterizing thin films, including specular and off-specular x-ray and neutron reflectivity, energy-dispersive x-ray reflectivity, total external reflectance x-ray fluorescence MeV ion scattering atomic force microscopy and ellipsometry. See, for example, Lin et al., *Proc. ACS PMSE* 77: 626 (1997); Wolf et al., *Silicon Processing for the VLSI Era*, Volume 1 (Process Technology) (Lattice Press, Sunset Beach, Calif. 1986), incorporated herein by reference.

Film thickness can be determined using commercially available instruments such as a Nanospec AFT. Correction of film thickness for refractive index is frequently desirable. Refractive index of thin films can be measured using an elipsometer. Such devices are commercially available (Rudolph). Other methods exist to characterize surface roughness, film integrity, dielectric constant and the like. These methods are briefly described below. It is well within the abilities of one of skill in the art to choose an appropriate method for determining a desired characteristic of a film of the invention.

The out-of-plane thermal expansion of the thin films can be measured using a capacitance cell. The sample is used to measure the capacitance of a precision parallel-plate capacitor of constant area so that the measured capacitance is inversely proportional to the actual sample thickness. These measurements are typically made under conditions of controlled humidity.

The surface roughness of films occurs as a result of the randomness of the deposition process. Real films almost always show surface roughness, even though this represents a higher energy state than that of a perfectly flat film. Depositions at high temperatures tend to show less surface roughness. This is because increased surface mobility from the higher substrate temperatures can lead to filling of the peaks and valleys. On the other hand, higher temperatures can also lead to the development of crystal facets, which may continue to grow in favored directions, leading to increased surface roughness. At low temperatures, the surface roughness as measured by surface area, tends to increase with increased film thickness. Oblique deposition that results in shadowing, also increases surface roughness. Epitaxial and amorphous deposits have shown measured surface area nearly equal to the geometrical area, implying the existence of very flat films. This has been confirmed by Scanning Electron Micrography (SEM) examination of these films. Thus, in a preferred embodiment, the surface roughness of the films of the invention is investigated by SEM and/or AFM. In a preferred embodiment, thin films of the invention are characterized further by being uniform and crack-free when viewed by electron micrography.

Infrared spectroscopy is also useful to characterize the films of the invention. For example, FTIR spectroscopy can provide information regarding the structure of films formed at different cure temperatures. Different cure temperatures will frequently produce films having different IR spectra. Moreover, infrared spectroscopy can be used to determine the silanol content of the thin film.

The organization of the film into a crystalline or amorphous structure can be determined using X-ray diffraction.

The density of the films of the invention can be varied by selection of the film precursors. Porosity develops during crosslinking of silsesquioxane molecules during the curing stage. The porosity of condensed silsesquioxane films is known to be a function of cure temperature: both thickness and porosity decrease with increasing cure temperature due to densification. The density of a thin film provides information about its physical structure. Density is preferably determined by weighing the film and measuring its volume. If a film is porous from the deposition process, it generally has a lower density than the bulk material.

The dielectric constant of a particular film can be measured by the MOSCAP method which is known to one of skill in the art. When the film is a component of a device with interconnect lines, the line-to-line capacitance measurements can be carried out, for example, by using a 0.50/0.50 $\mu$m width/spacing comb structure. Other methods for measuring dielectric constants can be applied to the films of the present invention.

Substrate

The choice of substrates to be coated is limited only by the need for thermal and chemical stability at the temperature and in the environment of the deposition vessel. Thus, the substrate can be, for example, glass, metal, plastic, ceramic or the like. It is particularly preferred herein, however, to coat electronic devices to provide a rotective or dielectric coating.

In an exemplary embodiment, the substrate is a semiconductor substrate (e.g., of silicon). The substrate is functionalized with conductors which may be, for instance, formed of an aluminum-0.5% copper alloy. The dielectric films of the present invention need not be deposited directly over a conducting layer (i.e., other dielectric layers may intervene or a conducting layer may not be present below the dielectric film of the present invention). In general, the dielectric film is deposited by, e.g., CVD of a silsesquioxane film precursor over the substrate, followed by reflow and film curing steps, which may be combined to convert the film to a final form. Either during reflow or curing (or between these steps), the film is typically subjected to a temperature between 120° C. and 200° C. for a period of time sufficient to produce silsesquioxane reflow and enhance the planarization of film.

In those substrates having interconnect lines, a metal layer is deposited and etched to form interconnect lines. Any number of interconnect lines and interconnect line geometries can be present. Interconnect lines typically have a vertical thickness on the order of 0.5–2.0 micron and a horizontal thickness which varies by design, but will typically be in the range of 0.25 to 1 micron. After the formation of interconnect, a thin layer of a film of the invention or another film (e.g., silicon dioxide) with a thickness on the order of 0.2–5.0 micron can optionally be deposited over the surface of the structure.

Objects Incorporating the Films

In another aspect, the invention provides an object comprising a low k dielectric film, said film comprising a material having the formula $[H_aSiO_b]_c[(R^1)_aSiO_b]_d[(R^2)_aSiO_b]_n$. In this formula $R^1$ and $R^2$ are members independently selected from $C_1$ to $C_{100}$ alkyl groups; a is less than or equal to 1; b is greater than or equal to 1.5; and c, d and n are members independently selected from the group consisting of the integers greater than 10. Although the films of the invention can be incorporated into essentially any device or object in which a low k dielectric film would have utility, in a preferred embodiment, the object comprises a wafer, preferably made of a material acting as a semiconductor.

Semiconductor wafers made of a variety of materials are well known in the art and substantially all of these wafers are appropriate for coating with the films of the invention. In a preferred embodiment, the comprises a member selected from Si, SiON, SiN, SiO$_2$, Cu, Ta, TaN and combinations thereof, more preferably Si, SiO$_2$ and combinations thereof.

In another preferred embodiment, the wafer is metallized, preferably with a member selected from copper, titanium, titanium nitride and combinations thereof.

It is understood that the examples and embodiments described herein are for illustrative purposes only and that various modifications or changes in light thereof will be suggested to persons skilled in the art and are to included within the spirit and purview of this application and are considered within the scope of the appended claims. All publications, patents, and patent applications cited herein are hereby incorporated by reference in their entirety for all purposes.

What is claimed is:

1. A low k dielectric film comprising a material having the formula

$[H_aSiO_b]_c[(R^1)_aSiO_b]_d[(R^2)_aSiO_b]_n$, wherein $R^1$ and $R^2$ are members independently selected from $C_1$ to $C_{100}$ alkyl groups;

a is less than or equal to 1;

b is greater than or equal to 1.5; and c, d and n are members independently selected from the group consisting of the integers greater than 10.

2. The method according to claim 1, wherein $R^1$ and $R^2$ are independently selected from $C_1$ to $C_{20}$ straight- or branched-chain alkyl group.

3. The method according to claim 2, wherein $R^1$ and $R^2$ are independently selected from $C_1$ to $C_{16}$ straight-or branched-chain alkyl groups.

4. The method according to claim 3, wherein $R^1$ and $R^2$ are independently selected from $C_1$ to $C_6$ straight-or branched-chain alkyl groups.

5. The method according to claim 4, wherein $R^1$ and $R^2$ are both methyl groups.

6. The film according to claim 1, wherein said film is a porous film.

7. The film according to claim 1, wherein said film has a dielectric constant of from about 2 to about 3.

8. A method for preparing a porous low k dielectric film having a preselected degree of porosity, said film comprising a material having the formula $[H_aSiO_b]_c[(R^1)_aSiO_b]_d[(R^2)_aSiO_b]_n$, wherein $R^1$ and $R^2$ are members independently selected from $C_1$ to $C_{100}$ alkyl groups;

a is less than or equal to 1;

b is greater than or equal to 1.5; and c, d and n are members independently selected from the group consisting of the integers greater than 10, said method comprising:

(a) depositing a film precursor to form a deposited film precursor, said film precursor comprising a material having the formula

$[R-SiO_{1.5}]_x[H-SiO_{1.5}]_y$, wherein x+y=n;

n is an integer between 2 and 30;

x is an integer between 1 and n;

y is a whole number between 0 and n;

R is a $C_1$ to $C_{100}$ alkyl group; and (b) curing said deposited film precursor to form a low k dielectric film with a preselected degree of porosity.

9. The method according to claim 8, wherein said curing is carried out using a method selected from the group of heat, ultraviolet light and combinations thereof.

10. The method according to claim 9, wherein said curing is carried out by heating to a temperature of from about 150° C. to about 700° C.

11. The method according to claim 10, wherein said temperature is from about 200° C. to about 500° C.

12. The film according to claim 8, wherein said low k dielectric film has a dielectric constant of from about 2 to about 3.

13. An object comprising a low k dielectric film, said film comprising a material having the formula:

$[H_aSiO_b]_c[(R^1)_aSiO_b]_d[(R^2)_aSiO_b]_n$, wherein $R^1$ and $R^2$ are members independently selected from $C_1$ to $C_{100}$ alkyl groups;

a is less than or equal to 1;

b is greater than or equal to 1.5; and c, d and n are members independently selected from the group consisting of the integers greater than 10.

14. The object according to claim 13, wherein said object comprises a wafer.

15. The wafer according to claim 14, wherein said wafer comprises a member selected from Si, SiON, SiN, SiO$_2$, Cu, Ta, TaN and combinations thereof.

16. The wafer according to claim 14, wherein said wafer is a member selected from Si wafers, SiO$_2$ wafers and combinations thereof.

17. The wafer according to claim 16, wherein said wafer is metallized.

18. The metallized wafer according to claim 17, metallized with a member selected from copper, titanium, titanium nitride and combinations thereof.

* * * * *

UNITED STATES PATENT AND TRADEMARK OFFICE
CERTIFICATE OF CORRECTION

PATENT NO. : 6,472,076 B1
DATED : October 29, 2002
INVENTOR(S) : Nigel Hacker

It is certified that error appears in the above-identified patent and that said Letters Patent is hereby corrected as shown below:

Title page,
Item [74], *Attorney, Agent, or Firm*, replace "Rutland & Tucker, LLP" with
-- Rutan & Tucker, LLP --.

Signed and Sealed this

Eighteenth Day of February, 2003

JAMES E. ROGAN
*Director of the United States Patent and Trademark Office*